US005749372A

United States Patent [19]
Allen et al.

[11] Patent Number: 5,749,372
[45] Date of Patent: May 12, 1998

[54] METHOD FOR MONITORING ACTIVITY AND PROVIDING FEEDBACK

[76] Inventors: Richard P. Allen, 110 Glen Oban Dr., Arnold, Md. 21012; David T. Krausman, #1 Ridgecliff Ct., Kingsville, Md. 21087

[21] Appl. No.: 397,585

[22] Filed: Mar. 2, 1995

[51] Int. Cl.$^6$ .................................. A61B 5/103
[52] U.S. Cl. .................... 128/782; 482/8; 482/900
[58] Field of Search ........................ 128/774, 782; 482/8, 900

[56] References Cited

U.S. PATENT DOCUMENTS

| | | | |
|---|---|---|---|
| 3,642,276 | 2/1972 | Kropf | 272/57 R |
| 3,788,647 | 1/1974 | Evans | 273/186 A |
| 4,112,926 | 9/1978 | Schulman et al. | 128/2 S |
| 4,117,834 | 10/1978 | McPartland et al. | 128/2 S |
| 4,353,375 | 10/1982 | Colburn et al. | 128/782 |
| 4,409,992 | 10/1983 | Sidorenko et al. | 128/782 |
| 5,001,632 | 3/1991 | Hall-Tipping | 364/413 |
| 5,125,412 | 6/1992 | Thornton | 128/670 |
| 5,391,080 | 2/1995 | Bernacki et al. | 434/254 |
| 5,490,816 | 2/1996 | Sakumoto | 482/8 |

Primary Examiner—Max Hindenburg
Attorney, Agent, or Firm—Oppenheimer Poms Smith

[57] ABSTRACT

A method and apparatus for accurate and convenient feedback to a user concerning activity level performance. Features of the invention include visual and audible outputs indicating a current level of activity. Another feature includes varying the rate of an audible tone output to reflect an actual and current activity level. In one embodiment an audible outputs is provided when a user's activity level reaches a desired minimum threshold within a given period of time. These features provide immediate and reliable feedback to a user for improved maintenance of at least a desired level of activity.

15 Claims, 4 Drawing Sheets

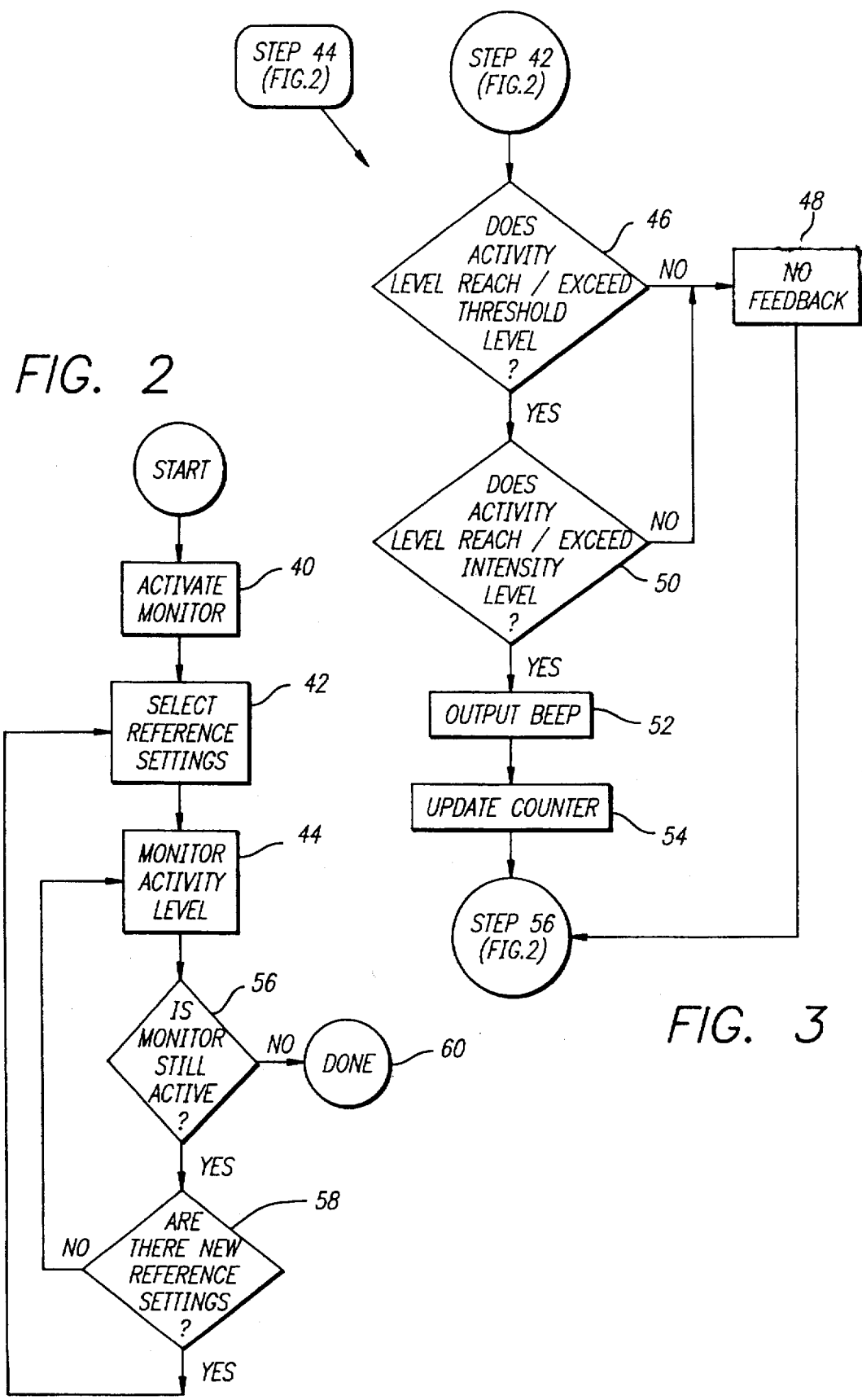

METHOD FOR MONITORING ACTIVITY AND PROVIDING FEEDBACK

BACKGROUND OF THE INVENTION

1. Field of the Invention

The present invention relates generally to monitoring levels of personal activity such as exercise, and, more specifically, to providing feedback to a user when a threshold level of activity is achieved.

2. Description of the Related Art

General awareness of the value of a healthy lifestyle, including a well-balanced diet and regular exercise, has increased in recent years. As a result of the increased awareness, many people have learned to restrict their calorie and fat intake on a daily basis while others have increased their level of exercise. While some people are highly self-motivated in their efforts, others require additional support.

Nutritional counselors and controlled meal selections typically assist dieters struggling to shed unwanted weight. Physical fitness trainers similarly help many of these people using exercise to become more physically fit by providing feedback and encouragement. However, personal trainers are often expensive, so that individual exercisers are usually unable to receive the personal support of a qualified trainer. Many individuals undertaking a new exercise regime often lack the luxury of an observer able to provide guidance on their performance and progress.

Previous attempts to provide a device offering objective guidance on an individual's activity level during exercise have suffered from various limitations. Typically such devices may include a display mechanism for indicating a totality of activity accomplished such as, for example, the total number of calories burned, the total distance traveled, or the cumulative time spent performing some activity. Further, attempts to provide better accuracy in whatever measure of activity relied upon (e.g. calories burned) often complicate use of the device. By way of example, calorie indicators typically require many user inputs, such as height, and weight for a more accurate estimation of a user's calorie expenditure during an activity. Further these devices also typically lack convenient progress and performance tracking. Individual exercisers are often required to keep some form of personal diary with a record of displayed outputs after each exercise session to monitor their performance level and collect consistent feedback.

Some electronic devices, such as that disclosed in U.S. Pat. No. 4,353,375 issued to Colburn, et al., include memory components to store a form of cumulative activity level data. The Colburn device allows a study of changes in the activity levels of a user over extended periods in order to monitor individuals with behavioral disorders. However, the Colburn device only collects data in memory for retrieval and study at a later time and does not provide data instantaneously to a user.

A need remains for an alternative form of providing activity guidance to an individual exerciser in a device that is accurate, compact, and which provides immediate feedback of a user's activity level. The present invention fulfills this need.

SUMMARY OF THE INVENTION

Accordingly, the present invention provides a method and apparatus for accurate and convenient audible feedback to a user indicative of the user's maintenance of a desired and current level of activity performance. The inventors have determined that use of an audible feedback in the present invention to indicate a user's performance of at least a minimum level of activity greatly reduces the amount of attention a user must direct to the rate of activity performance. Beginning and otherwise sedentary users embarking on a new physical activity program find that the form of audio feedback provided by the present invention encourages both continued participation in the activity program, and a more uniform level of higher performance in the activity program. The invention may also include an LCD (liquid crystal display) indicating cumulative activity achievement. Another feature of the present invention includes varying the rate of an audible output tone to reflect an actual and current activity level. Alternatively, or additionally, an audible output tone is provided when a user's activity level reaches a desired minimum threshold within a brief preset time period. In another aspect of the present invention, the LCD provides a total visual account of feedback activity and allows a user to track an activity level above a threshold level. These features provide immediate and reliable feedback to a user for improved maintenance of at least a desired level of activity.

BRIEF DESCRIPTION OF THE DRAWINGS

The present invention, together with further objects and advantages thereof may best be understood by reference to the following description taken in conjunction with the accompanying drawings in which:

FIG. 2 is a flow diagram illustrating an overall method in accordance with another aspect of the present invention;

FIG. 3 is a flow diagram illustrating a method for the step illustrated at 44 of FIG. 2;

DETAILED DESCRIPTION OF THE INVENTION

Figure 1A:
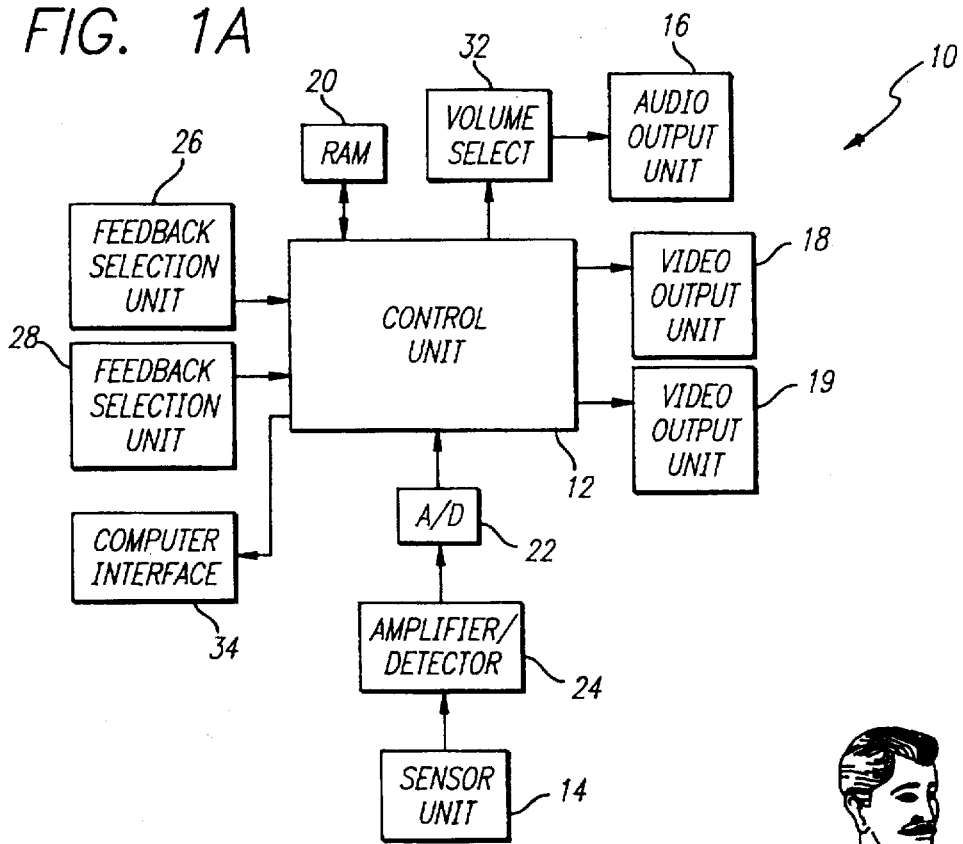
FIGS. 1A and 1B are block diagrams illustrating a structure for an activity monitor in accordance with one aspect of the present invention.

The present invention allows a person to monitor their current and instantaneous activity level, e.g. a level of exercise, with direct and instantaneous audible feedback on a current level of performance. In accordance with the present invention a small device is attached to a user's body, such as the waist area, that senses accelerations or movements of the user. In accordance with one significant aspect of the present invention, an audible feedback provides a beep tone when a user reaches or exceeds a minimum threshold number of accelerations or movements during a brief, predetermined time interval. This audible feedback advises a user that a minimum level of performance has been achieved and is being maintained during the course of that time interval of performance.

In one embodiment, the structure of the present invention includes a piezoelectric transducer device acting as a sensor of the user's acceleration and a control unit including a microcontroller for operation of the monitor and the feedback. The device senses an acceleration induced by the user's activity. If a single transducer sensor is used, the monitor is most sensitive to a single plane of body motion, i.e., up and down movement. In yet another embodiment, a dual piezoelectric transducer arrangement is used to sense accelerations induced by a user's body movement in three orthogonal dimensions, i.e., up and down, back and forth as well as side to side. Examples of such activities could include walking, jogging, or aerobic exercise. As used herein a desired activity level corresponds to a number of accelerations or movements per unit of time. Walking, for example, may induce a 0.25 g acceleration per step. A walking activity level corresponding to three miles an hour would thus, for example, induce four accelerations every three seconds. Each of these accelerations would be approximately 0.25 g's in magnitude. An audible feedback beep tone would then be generated, in accordance with the present invention, so long as a minimum of four accelerations were sensed every three second interval, indicating the user's maintenance of a desired walking speed. The feedback unit may also include a liquid crystal display (LCD) so as to provide a visual feedback of a user's activity level.

The present invention provides a user with accurate, virtually instantaneous and continuing feedback on their current level of activity through an audible feedback technique that requires less of the user's attention to monitor. Use of an audible feedback output in the present invention has been found by the inventors to offer a clear indication of current activity levels and maintenance of a desired minimum level of activity performance without requiring a user's focused attention to the feedback mechanism itself. The inventors have found visual activity performance indicators typically require an undesirably high degree of a user's attention to consistently watch the output level and maintain a desired activity level. By providing an audible feedback, and by providing this feedback only when a minimum desired activity level is achieved and maintained, the monitor of the present invention frees a user to direct more of their attention to other matters. The inventors have also determined that this aspect of the present invention can significantly reduce or eliminate an unpleasant tedium associated with performing a desired physical activity at some specified rate of achievement. Reducing this tedium has been found by the inventors to be particularly helpful to users who are normally sedentary and are only starting out on some conservative form of physical exercise. By reducing the tedium associated with maintaining a desired minimum level of activity, the inventors have found the present invention dramatically increases the regularity with which ordinarily sedentary beginners perform desired physical exercise activities along with the actual level of exercise performed by these beginners.

The intensity level of activity initiating the audible performance feedback may be varied in the present invention. For example, a minimum intensity level at which audible feedback is provided may be adjusted according to a user's level of physical fitness. In addition, an alternate embodiment of the present invention provides a longer time period of data accumulation for a more cumulative indication of a user's prolonged activity level.

The adjustable features of the invention further provide continual flexibility and "feedback training". The "training" occurs as a user changes the feedback settings according to their activity improvements and increases in endurance. Thus for example, when a user starts a walking exercise program, the present invention may be initially calibrated to provide audible feedback at a walking rate of two miles per hour. Thereafter, once the user's activity performance level has increased, the invention may be adjusted to provide audible feedback at a rate of four miles per hour. In yet another embodiment of the present invention, the audible feedback may alternatively reflect a sensed level of activity increase, or acceleration, by changing the character of audible feedback with increase in activity levels. As the user's activity level increases, a rate of audible output beep tones may, for example, increase. This additional feature of the present invention has also been found to provide further useful information to a user concerning their activity level that again requires a minimum of the user's attention. Some users, typically only beginning some modest form of physical activity, find this feature allows the user to more easily achieve and maintain a desired activity level without requiring all of the user's focused attention. The adjustable features and other features of the invention are presented in more detail in the description of the following figures.

FIG. 1 illustrates a block diagram of one embodiment of an activity monitor 10 in accordance with the present invention. The monitor includes a control unit 12, activity sensor units 14 and 15, and audio output unit 16. Further included are visual display counter units 18 and 19, random access memory unit 20, analog-to-digital convertor unit 22, amplifier detector 24, and feedback selection units 26 and 28. A volume control 32 and computer interface 34 are also included. The details of the monitor shown in FIG. 1 are provided in conjunction with the description of FIGS. 2–5.

An embodiment of one method of the present invention is illustrated in FIG. 2. Preferably, the monitor 10 is housed in a small pager-like device and attached snugly on the waist of a user with a belt attachment. Use of a belt attachment frees the user from having to hold the monitor or otherwise inconveniently support the monitor while performing an exercise activity. Other convenient manners of attachment are also suitable, such as support of the monitor in a pocket. The inventors have determined, however, that accelerations of the user's body associated with many forms of physical activity are more accurately measured if the monitor 10 is preferably positioned midway between the midline of the waist and the outer edge of a nondominant hip of the user.

Activation of the monitor 10 is suitably performed by selection of a slide power switch (not shown). Lithium batteries (not shown) may be used to provide long term power to the monitor 10. Conservation of the battery supply is achieved by switching off monitor 10 when not in use.

Following activation of the monitor 10, the method of the present invention (FIG. 2) continues with a step 42 concerning selection of reference settings for monitor 10. By way of example, feedback selection units 26 and 28 are switches controlled by a user. Selection unit 26 suitably provides an immediate feedback sensitivity selection switch. With selection unit 26, a user preferably indicates a minimum activity intensity level required to initiate feedback. A threshold acceleration sufficient to indicate activity performance by the user, is preferably preselected in the monitor design. A selected threshold acceleration level of 0.1 g (where g is 9.8 m/sec/sec, the acceleration due to gravity) has been found by the inventors to work well for distinguishing accelerations caused by performance of the physical activity from movement not related to performance of the physical activity. For example, a 0.1 g acceleration threshold level has been found to allow accurate monitoring of a range of user activities equivalent to walking at speeds of about 1–4 mph. of course, other levels of acceleration may be more suitable for monitoring forms of user activity other than walking. For example, 0.01 g would be suitable for geriatric monitors, i.e., for use with people having reduced levels of acceleration during performance of modest exercise activity. Conversely, 0.5 g has been found by the inventors to be more suitable for monitoring activities corresponding to higher acceleration activities, such as high impact aerobics.

In one embodiment of the present invention selection unit 26 is a nine position DIP (dual in-line package) switch that provides ten different settings for indication of the level of activity intensity required to initiate audible feedback. These settings may indicate a total number of times within a one second period that a user must reach or exceed a minimum acceleration in order to initiate feedback. In one embodiment, a low level of activity equivalent to a sedentary user performing household chores is set to correspond to a selection of one of settings of 1–3. A moderate level of intensity equivalent to a user undertaking moderate walking is set to correspond to a setting of 4–6. A high level of intensity equivalent to rigorous exercise, such as vigorous walking, in turn corresponds to a setting of 7–9. Thus, for example, a setting a of 3 indicates that a user must achieve the minimum level of acceleration or movement three times within the one second time interval in order to receive an audible feedback beep tone. A switch with a higher number of settings may also be used to provide a larger range of activity intensity levels (e.g. requiring twenty accelerations or movements within a one second interval) without departing from the spirit of the present invention.

In an alternate embodiment of the present invention, selection unit 26 is a single push button. A push button selection unit allows a user to select a setting by simply pressing down on the push button. In a preferred embodiment, each time a user presses the push button, the setting is increased by one. Again, a range of settings from 0 to 10 has been found by the inventors to work well by providing a wide range of potential activity levels corresponding to activity monitor applications ranging from modest activity performances associated with beginning users to substantially higher activity levels associated with regular athletes.

Selection unit 28 is preferably a ten position slide switch used to select a minimum activity value for the cumulative performance feedback aspect of the present invention. With selection unit 28, a user selects a total number of activity counts that must be maintained over a longer time interval, such as thirty seconds, in order to initiate an audible feedback indicative of the user's cumulative activity performance over this longer time interval. The cumulative audible feedback preferably provides an output tone distinguishable from the output tone of the instantaneous feedback. A rapid output of four successive beeps in a total period of time of about 1.5 seconds has been found by the inventors to work well as a cumulative feedback audible output tone. Use of audible cumulative feedback has also been found to work well under circumstances requiring maintenance of an activity level over a wider period of time, such as during physical rehabilitation training.

A RAM unit 20 is included in the monitor 10 (FIG. 1) to store activity data for comparison purposes using the selected cumulative feedback level, multiplied by a scaling factor. By way of example, with an initial scaling factor of twenty, selection of position 2 on the slide switch could correspond to an activity count of 40 counts over the cumulative time interval. This 40 counts would correspond to sustenance of the required activity intensity level for a total of 40 counts over a given period of time, e.g. thirty seconds. Selection of position 0 on the slide switch suitably deactivates cumulative feedback. In one embodiment of the invention the RAM unit 20 preferable has the capacity for storing 32 k bytes of data.

Once the feedback settings are selected, the method of the present invention continues with step 44 of monitoring a user's activity level. Further sub-steps implemented in performing step 44 in one preferred embodiment of the present invention are presented in the flow diagram of FIG. 3. The step of monitoring (step 44 in FIG. 2) begins in this embodiment with sub-step 46 and a determination of whether the user's motion has reached or exceeded a minimum level of acceleration. As explained previously, this minimum acceleration level is preferably preselected in the design of the monitor and, for illustration purposes, is set at 0.1 g. If this minimum acceleration is not reached or exceeded by the user's motion, no feedback is provided, as shown in step 48. If minimum acceleration is reached or exceeded by the user's motion, i.e., when a user's movement induces an acceleration of the device at or above, for example, 0.1 g, the method continues with step 50 of determining whether the activity level has reached or exceeded the intensity set by selection unit 26. As explained above, the activity intensity level is the required number of times within a 1 second period a user must move at or above the minimum acceleration in order to provide audio feedback indicative of a minimum activity performance. If the activity intensity level is not reached or exceeded, no feedback is provided, as indicated in step 48. Thus if a minimum activity performance level were set to correspond to, for example, walking at a rate of three miles per hour, then a user's activity performance level of walking at two miles per hour would be insufficient to trigger an audible feedback. The absence of this feedback would indicate to the user an insufficient activity performance, notifying the user by the absence of feedback that a faster walking speed was required.

When the minimum activity performance level is reached or exceeded by the user, the method continues with the feedback output. In step 52, an audible output beep tone is provided. Preferably, the audio output unit 16 provides an output beep as a 2400 Hz (Hertz) tone of 78 decibels (Db) for a period of 100 milliseconds at the end of the monitoring interval. Alternatively, the frequency of the tone is variable in a range of approximately 50 Hz to 10,000 (10 k) Hz. For instantaneous feedback, the period of monitoring is approximately one second. For cumulative feedback, the period of monitoring is preferably approximately thirty seconds and the same output tone is provided four consecutive times. The output tone described has been found to work well as a feedback indicator of a sufficient sound level without being a distraction or annoyance to a user. The inventors have also found that the one second and thirty second time intervals work best for providing continuous and cumulative feedback concerning a user's performance. A piezo type beeper such as an Intervox BRT 1209P-06 has also been found to work well as audio output unit 16.

A volume control unit 32, such as a four position DIP switch, may be included in order to allow a user to increase or decrease the volume of the audible output beep tone as desired. By way of example, selection of switch 1 provides output at the highest volume while selection of switch 3 provides output at the lowest volume. No selection of a volume level switches the volume of the audio feedback off.

Further feedback is provided in step 54 with the update of the LCD counter units 18 and 19. A six-digit LCD display such as Red Lion Controls #SUB-CUB1 is suitable for the LCD counter units. Counter unit 18 preferably increases by one every time an output beep occurs in instantaneous use of the monitor 10. Counter unit 19 preferably outputs a total count of cumulative data corresponding to the cumulative use of the monitor 10. Although steps 52 and 54 are shown separately in FIG. 3, the two steps are preferably performed substantially instantaneously so as to be indistinguishable to a user. Of course, counter units 18 and 19 may be eliminated if only audible feedback is deemed necessary. Use of the counter units 18 and 19, however, may additionally provide a convenient account for a user on the total number of output tones achieved during a particular activity.

Such output tones may be the calories burned over a period of time or during a particular activity.

Upon completion of the feedback outputs in step 54, the method of the invention continues with step 56 (FIG. 2) of determining whether the monitor is still active. If it is still active, the method continues with step 58 and the determination of whether new reference settings have been selected. If new reference settings have been selected, the method returns to step 42 with the setting selection step. If no new reference settings have been selected (or upon completion of step 42) the method continues with step 44 and the monitoring of the activity level, as described above. Once the monitor is no longer active, as determined by step 56, the method is finished as represented by step 60.

The method steps described in conjunction with FIGS. 2 and 3 are suitably performed by a control unit 12, such as a microcontroller (FIG. 1). By way of example, a Signetics 87C751 microcontroller is suitable for use in the monitor 10. Internal programmable read only memory (PROM) preferably provides necessary storage of program steps in the present invention, as is well appreciated by those skilled in the art. Alternatively, low power discrete CMOS integrated circuit chips are also suitable as a control unit in the present invention, the design of suitable CMOS chips also being well understood by those skilled in the art.

A sensor unit 14 preferably performs the sensing of a user's movement by way of a piezo electric type transducer with a double plate ceramic element, such as a 61416 PZT-5A BIMORPH from Morgan Matrox Inc. The sensor unit 14 creates an analog signal with each accelerated or nonuniform movement by the user. The sensor output signal is amplified by a standard amplifier 24 and converted into a digital signal by an analog-to-digital (A/D) convertor 22 before input to control unit 12. In an alternate embodiment of the present invention, a second sensor unit 15 is included in the monitor 10.

Figure 1B:
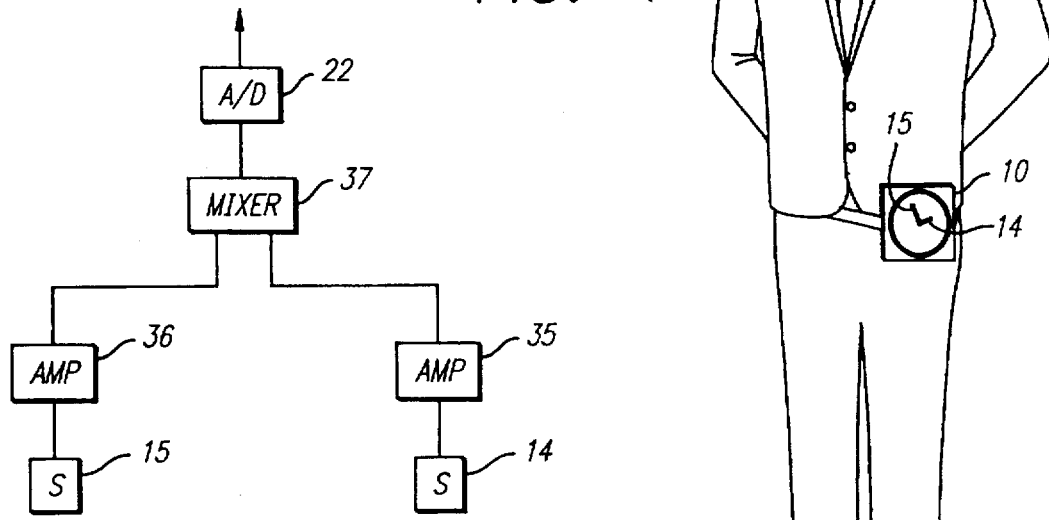

As illustrated in FIG. 1B in a dual sensor element arrangement, sensor units 14 and 15 are respectively electrically connected to amplifiers 35 and 36 input signals to the mixer 37 where the amplified signals of sensors 14 and 15 are electronically summed. The output from mixer 37 is input to the A/D convertor 22 as further discussed above. The arrangement of the sensor units 14 and 15 provides a greater range of sensitivity to a user's acceleration in multiple directions. Piezoelectric type transducers are typically most sensitive to accelerations or movements in a single plane, e.g., movement forward and backward. Providing two sensor units 14 and 15 in accordance with the present invention, however, can increase the range of sensitivity of the monitor to activity in three dimensions.

Figure 4:
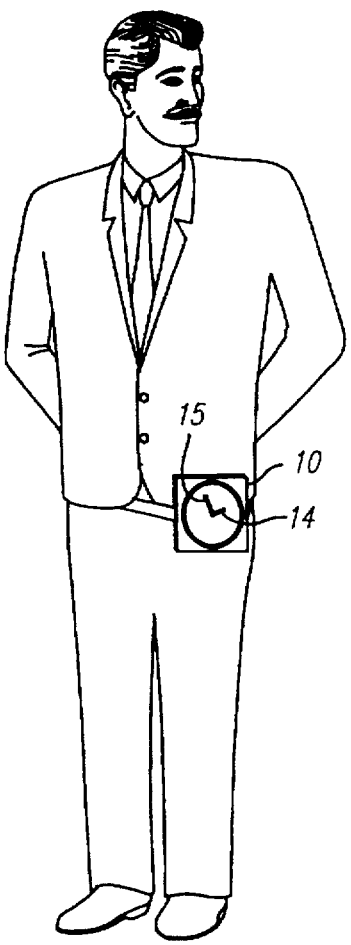
FIG. 4 illustrates positioning of the activity monitor in accordance with one aspect of the present invention.

FIG. 4 illustrates a preferred orientation of dual sensor units 14 and 15 in the monitor 10. As shown in FIG. 4, the monitor 10 has an overall vertical orientation when positioned at the waist in accordance with a preferred embodiment of the present invention. In accordance with a further aspect of the invention the dual sensor units 14 and 15 are preferably positioned within the monitor 10 to maximize sensitivity of the monitor 10 to a user's movements in multiple dimensions.

Figure 5A:
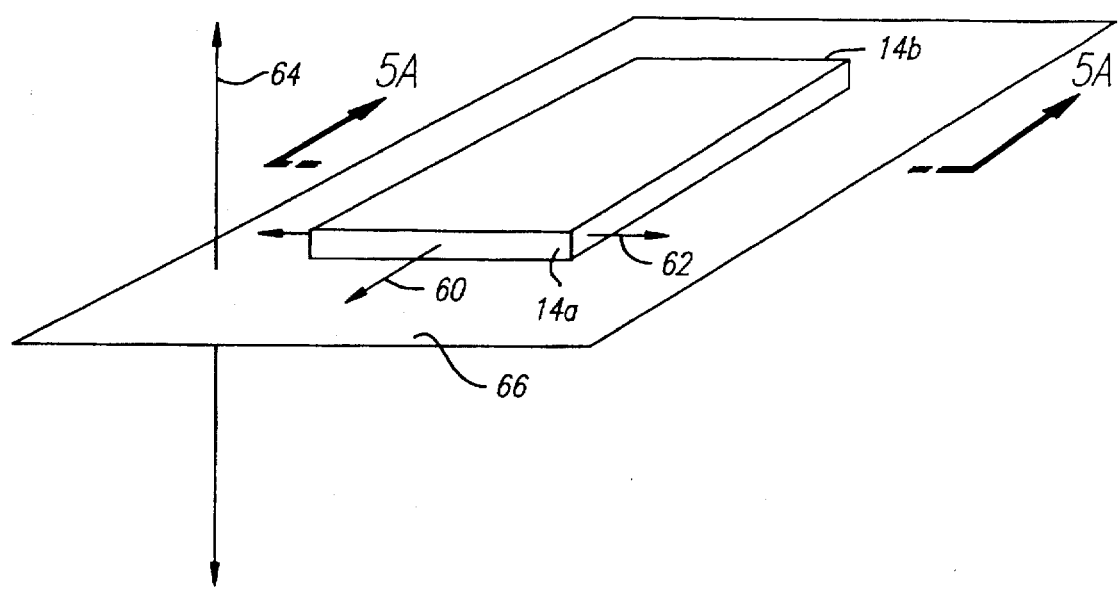
FIGS. 5A–5C illustrate an enlarged view of orientations for a dual sensor arrangement within the activity monitor in one embodiment of the present invention.
Figure 5B:
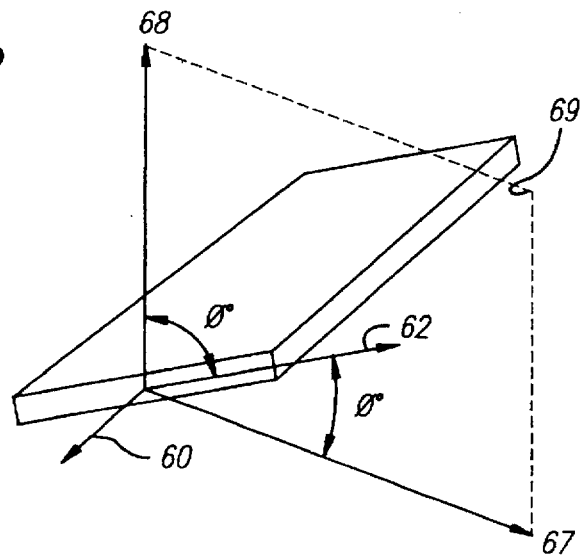
Figure 5C:
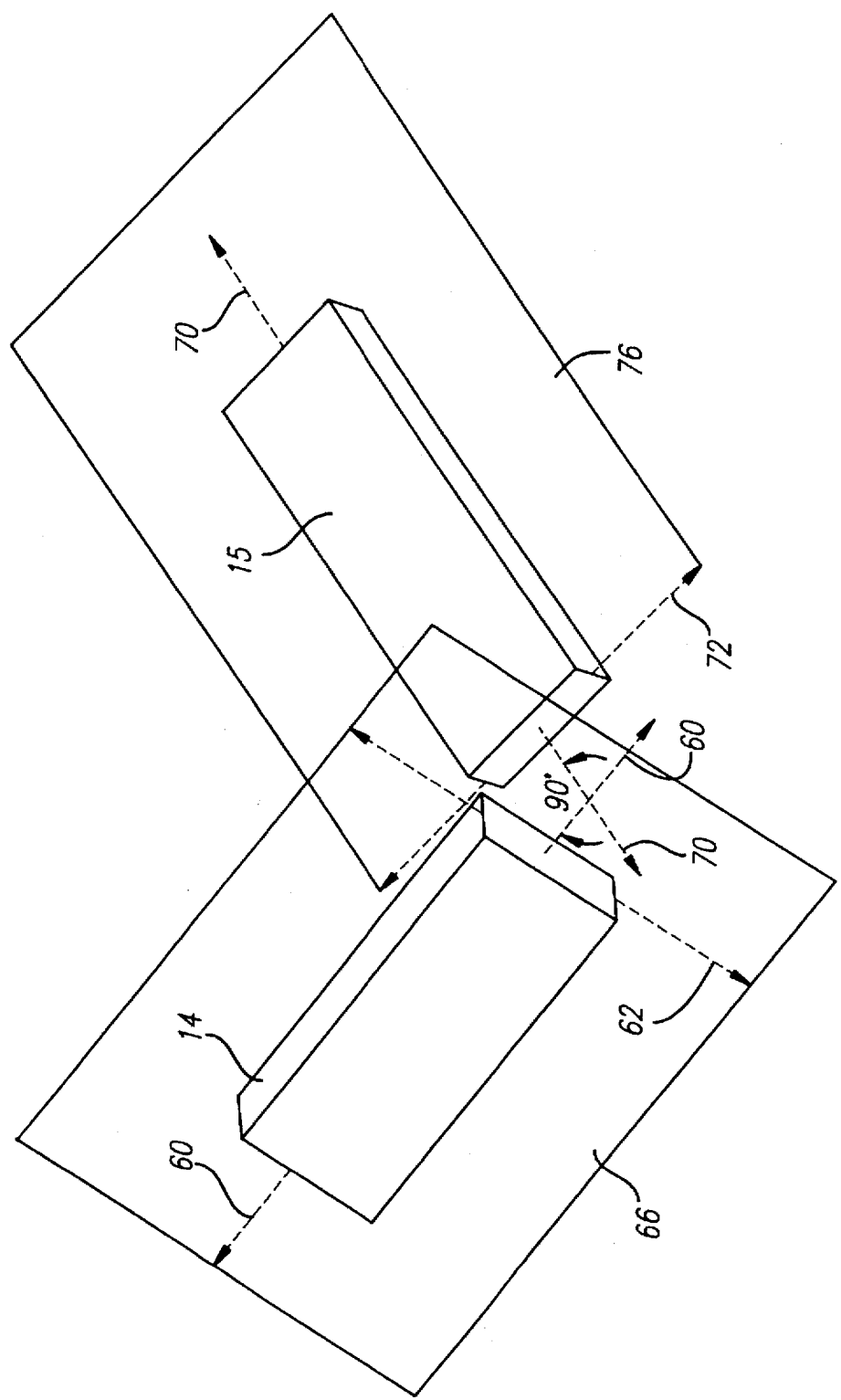

FIGS. 5A to 5C illustrate in greater detail a preferred orientation of the sensor units 14 and 15. As shown in FIG. 5A, an individual piezoelectric type sensor unit such as the sensor units 14 and 15 have a generally flat and rectangular configuration. Sensor 14 thus, for example, may be characterized as having a major or longitudinally oriented axis 60 and a minor or latitudinally oriented axis 62. Typically, sensor 14 would be secured at one end 14a with an opposing end 14b left free in space. This arrangement provides maximum sensitivity to accelerations or movements of the sensor 14 along a line 64 perpendicular to a plane 66 defined by the longitudinal axis 60 and latitudinal axis' 62 of the sensor.

The inventors have determined, however, that piezoelectric type sensors such as sensors 14 and 15 are, in fact, sensitive to accelerations or nonuniform movement along two orthogonal axis' instead of simply the single axis 64 oriented perpendicular to the plane 66 defined by the longitudinal and latitudinal axis' 60 and 62 of the sensor. As more clearly illustrated in FIG. 5B, accelerations and nonuniform movement of the sensor 14 may be sensed along two orthogonal sensing axis' 67 and 68 that form a plane 69 oriented perpendicular to the longitudinal axis 60 of the sensor 14 and parallel to the latitudinal axis 62 of the sensor 14. The inventors have determined that equal sensitivity to accelerations and nonuniform movement along either of sensing axis 67 or sensing axis 68 is observed when the latitudinal axis 62 of the sensor 14 is oriented at an angle theta of approximately 45° with respect to the sensing axis 67 and similarly oriented at an angle phi with respect to the sensing axis 68 of about 45°.

In accordance with a further aspect of the invention, only two sensors 14 and 15 are used to sense accelerations or nonuniform movement along three orthogonal axis' (i.e. in three dimensions) by orienting sensor 14 with respect to the sensor 15 so that the longitudinal axis' of the sensors 14 and 15 are oriented perpendicular to one another. The latitudinal axis' of each sensor is also oriented so as to intersect a plane formed by the longitudinal and latitudinal axis' of the other sensor at an angle that is neither perpendicular, nonparallel, to this plane.

In one preferred embodiment of the present invention the sensors 14 and 15 are oriented as illustrated in FIG. 5C. As shown, sensor 14 has a longitudinal axis 60 and latitudinal axis 62 forming a plane 66 and sensor 15 has a longitudinal axis 70 and latitudinal axis 72 forming a plane 76. As further illustrated in FIG. 5C, the longitudinal axis 62 of sensor 14 is oriented at a perpendicular angle to the longitudinal axis 70 of sensor 15. The latitudinal axis 62 of sensor 14, however, has a nonparallel and nonperpendicular orientation to the plane 76 formed by the longitudinal and latitudinal axis' 70 and 72 of sensor 15. Similarly the latitudinal axis 72 of sensor 15 has a nonparallel and nonperpendicular orientation to the plane 66 formed by the longitudinal and latitudinal axis' 60 and 62 of sensor 14. Again expressed in other terms, the sensors 14 and 15 are oriented with respect to one another so that their respective longitudinal axis' 60 and 70 are oriented roughly perpendicular to one another, and so that their respective latitudinal axis' 62 and 72 have a nonparallel orientation with respect to a plane formed by the orthogonally oriented longitudinal axis' 60 and 70.

In this orientation sensors 14 and 15, in combination, sense accelerations in directions parallel to either longitudinal axis 60 of sensor 14 or the orthogonally oriented longitudinal axis 70 of sensor 15 (i.e. in two dimensions). That is, sensor 15 will sense accelerations or nonuniform movement parallel to the longitudinal axis 60 of sensor 14 and sensor 14 will sense accelerations and the like parallel to the longitudinal axis 70 of sensor 15. Both sensors 14 and 15, however, also sense accelerations along an axis roughly perpendicular to the plane formed by the longitudinal axis' 60 and 70 of the sensors 14 and 15 (i.e. in a third dimension). This sensitivity to accelerations and nonuniform movement perpendicular to the plane formed by the longitudinal axis' 60 and 70 of the sensors 14 and 15 is attributable to the orientation of the latitudinal axis' 62 and 72 of the sensors 14 and 15.

The inventors have further determined that when sensors 14 and 15 are connected to a mixing circuit 37 as illustrated in FIG. 1B, the latitudinal axis' 62 and 72 of sensors 14 and 15 are preferably oriented at an angle approximately 25° from a generally vertically oriented axis perpendicular to the generally horizontal plane formed by the longitudinal axis' 60 and 70 of the sensors 14 and 15. It is believed by the inventors that this particular angular orientation accommodates torques imposed on the sensors 14 and 15 in a vertical plane by the force of gravity. While the various angular orientations discussed above have been found by the inventors to be optimum, it should still be appreciated by those skilled in the art that other orientations could be employed without departing from the scope or spirit of this invention.

As noted above, the analog signal output from sensors 14 and 15 is first preferably amplified, electronically summed by mixer 37 and then converted by A/D convertor 22 to a digital signal. A/D convertor 22 may output signals used in a digital summing method in an alternate embodiment of the present invention. As further mentioned previously, as an alternative to the output of a single tone at the end of each second during instantaneous feedback, the rate of output tones may change with the rate of a user's activity performance level. By way of example, an intensity setting of four might establish the number of times a user would need to achieve the minimum acceleration level within the selected time interval to receive an output tone. With a digital summing method, as a user achieves an activity performance level higher than the selected performance level, e.g., the user reaches the minimum acceleration level six times in the selected time interval, rather than the required four times, more than one output tone occurs as an indication of the increased activity performance level. The digital summing method involves the integration of the signal supplied via the sensor unit 14 (and sensor unit 15 in a dual sensor embodiment), as will be readily understood by those skilled in the relevant arts.

RAM 20 preferably provides storage of activity data over several days in addition to the cumulative feedback function explained previously. For example, a 32K byte RAM chip has been found to work well in storage of minute-to-minute data for up to eleven days. The stored data allows further evaluation of the monitored activity levels for data analysis at a later time. Analysis and evaluation of activity levels over longer terms are typically useful in clinical studies of activity levels. Stored data is suitably downloaded to an external computer system via computer interface 34, as is well understood by those skilled in the art. Of course for a more simplified configuration, RAM 20 need not be included.

In an alternate embodiment of the present invention, activity data stored in RAM 20 or a count displayed on counter units 18 or 19 represents an equivalent quantified activity level. An activity count generated during a period of exercise, such as walking, jogging, or other aerobic activity, would correlate to a measured activity, such as walking on a motorized treadmill, through calibration of the device in clinical settings. By way of example, calibration can be performed by averaging activity count data for a test group, such as 80 individuals, when the monitor is worn for specified periods at specific levels of activity, e.g. walking on a treadmill in levels incremented by one mile per hour. Corresponding output data during the clinical studies is suitable to represent a baseline standard of information for an individual using the monitor. As an example, a count of 200 achieved by an individual user might correlate to walking on a treadmill at a speed of 2 mph for 10 minutes. The baseline information provides an easily understood equivalent to a user by correlating the user's level of activity during a chosen activity to a level of activity (i.e., a time and speed) of a well understood activity. Of course, activities other than walking on a treadmill are suitable for calibration of the monitor, but preferably, the chosen activity for calibration is well known and generally well understood by an average user.

Although several embodiments of the present invention have been described, it should be understood that the present invention may be embodied in many other specific forms without departing from the spirit or scope of the invention. Particularly, the feedback has been described in terms of a tone and may be replaced by components to deliver recorded voice messages, such as "Very good" or "Keep it up!" to inform the user of their performance. Alternatively, a continuous output tone is also a suitable feedback. Preferably, the frequency and amplitude of the tone signal changes according to the activity level. For example, as the user's activity level increases above the threshold level, the continuous output tone correspondingly increases in amplitude and frequency as an indication of the raise in the user's activity level. Suitably, if the activity level drops below the threshold level, no continuous tone is output.

Additionally, in an alternate embodiment of the present the monitor provides a cumulative count of accelerations without a threshold requirement. Suitably, selection of a zero setting on the slide switch or push button selection unit indicate a no threshold mode to the monitor. In this further aspect, the device preferably does not output audible feedback but alternatively does output a cumulative number of counts on the LCD for accelerations in the range of, for example, 0.001 g to 10 g. Preferably, the cumulative number of counts is not a total number of electrical signals generated by the sensor unit(s), but is a scaled number representative of the total number of electrical signals. By way of example, a total number of electrical signals equal to 1000 is suitable as an equivalent to an output of a 1 on the LCD in the no threshold mode. Each time the total number of electrical signals in put to the monitor increases by 1000, the output count increases by 1. Of course, the use of 1000 is merely one example and other reference counts are suitable. Therefore, the present examples are to be considered as illustrative and not restrictive, and the invention is not to be limited to the details given herein, but may be modified within the scope of the appended claims.

What is claimed is:

1. A method for monitoring a user's exercise performance, a method comprising:
   providing portable monitor sensing and recording means for sensing a user's exercise level and cumulative exercise accomplishment for a preselected time interval, providing visual feedback of acceleration of physical body movements by the user, providing audible feedback of said acceleration of physical body movements by the user, and recording the total amount of acceleration of physical body movements of said user for a predetermined time period.

2. A method as recited in claim 1 wherein said means further converts digital integration of body acceleration of the user to quantify body movements.

3. A method as recited in claim 1 further comprising the step of converting body movements of the user to acceleration of physical body movements by the user recorded by said means.

4. A method as recited in claim 1 further comprising the step of converting said acceleration of physical body movements by the user to calories burned based on the user's weight.

5. A method as recited in claim 1 further comprising the step of providing said audible feedback in the form of a tone or beep based on a preselected level of exercise of said user.

6. A method as recited in claim 3 further comprising the step of providing said audible feedback in the form of a tone or beep based on a preselected quantity of acceleration of physical body movements by the user recorded by said means.

7. A method as recited in claim 4 further comprising the step of providing said audible feedback in the form of a tone or beep based on a preselected quantity of calories burned by the user.

8. A method as recited in claim 3 further comprising the step of providing said visual feedback in the form of a visual count on an LCD display of said means that corresponds to cumulative acceleration of physical body movements by the user recorded by said means.

9. A method as recited in claim 4 further comprising the step of providing said visual feedback in the form of a visual count on an LCD display of said means that corresponds to calories burned recorded by said means.

10. A method as recited in claim 1 further comprising the step of storing cumulative exercise data said means in a memory for later retrieval.

11. A method as recited in claim 3 further comprising the step of providing said audible feedback in the form of a tone or beep based on a preselected quantity of acceleration of physical body movements by the user recorded by said means.

12. A method as recited in claim 4 further comprising the step of providing said audible feedback in the form of a tone or beep based on each calorie burned by said user.

13. A method as recited in claim 1 further comprising the step of establishing at least one reference setting on said means as an indication of a minimum exercise level relating to said user.

14. A method as recited in claim 13 wherein the step of establishing at least one reference setting further comprises setting a count selector to indicate a minimum amount of acceleration of physical body movements by the user recorded by said means in a preselected time interval.

15. A self-contained method for monitoring a user's exercise performance carried out on portable equipment while said user is either moving from one place to another or exercising in place comprising:

the steps of sensing a user's exercise level and cumulative exercise accomplishment on said equipment for a preselected time interval;

providing visual feedback on said equipment of acceleration of physical body movements by said user;

providing audible feedback on said equipment of acceleration of physical body movements by said user; and recording the total amount of acceleration of physical body movements on said equipment for a predetermined period of time.

* * * * *